United States Patent [19]
Tomes et al.

[11] Patent Number: 5,877,400
[45] Date of Patent: Mar. 2, 1999

[54] TRANSGENIC METHODS AND COMPOSITIONS FOR PRODUCING PARTHENOCARPIC FRUITS AND VEGETABLES

[75] Inventors: Dwight T. Tomes, Cumming; Paul D. Miller, Granger; Robert J. Bensen, Grimes, all of Iowa

[73] Assignee: Pioneer Hi-Bred International, Inc., Des Moines, Iowa

[21] Appl. No.: 641,479

[22] Filed: May 1, 1996

[51] Int. Cl.[6] .......................... C12N 15/29; C12N 15/82; A01H 4/00; A01H 5/00

[52] U.S. Cl. .................................. 800/205; 800/DIG. 40; 800/DIG. 41; 800/DIG. 19; 800/DIG. 44; 536/23.6; 536/24.1; 536/23.7; 435/69.1

[58] Field of Search .......................... 800/205, DIG. 40, 800/DIG. 41, DIG. 19, DIG. 44; 536/23.6, 24.1, 23.7; 435/69.1, 320.1, 172.3, 240.4; 47/58

[56] References Cited

U.S. PATENT DOCUMENTS

| | | | |
|---|---|---|---|
| 4,242,120 | 12/1980 | Manankov | 71/89 |
| 5,254,801 | 10/1993 | Dotson et al. | . |
| 5,262,316 | 11/1993 | Engler et al. | 435/172.3 |
| 5,412,085 | 5/1995 | Allen et al. | 536/24.1 |
| 5,426,041 | 6/1995 | Fabijanski et al. | 435/172.3 |

FOREIGN PATENT DOCUMENTS

| | | | |
|---|---|---|---|
| 0 692 537 A2 | 1/1996 | European Pat. Off. | C12N 15/29 |
| WO 91/09957 | 7/1991 | WIPO | C12N 15/82 |
| WO 92/01799 | 2/1992 | WIPO | C12N 15/82 |
| WO 93/16096 | 8/1993 | WIPO | C07H 21/02 |
| WO 94/28141 | 12/1994 | WIPO | C12N 15/53 |
| WO 95/35383 | 12/1995 | WIPO | C12N 15/60 |
| WO 96/05317 | 2/1996 | WIPO | C12N 15/53 |
| WO 96/26639 | 9/1996 | WIPO | A01H 5/100 |

OTHER PUBLICATIONS

Wu, K., et al., "Molecular Cloning and Photoperiod–Regulated Expression of Gibberellin 20–Oxidase from the Long-–Day Plant Spinach", *Plant Physiol.* (1996) 110:547–554.

Phillips, A.L., et al., "Isolation and Expression of Three Gibberellin 20–Oxidase cDNA Clones from Arabidopsis", *Plant Physiol.* (1995) 108:1049–1057.

Bensen, R.J., et al., "Cloning and Characterization of the Maize An1 Gene", *The Plant Cell,* (1995) vol. 7, 75–84.

Jacobsen, S.E., et al., "Mutations at the Spindly Locus of Arabidopsis Thaliana Result in Gibberellin–Independent Growth and Development", *Supplement to Plant Physiology* (1993) vol. 102, No. 1, p. 8, Abstract 35.

Twell, D., et al., "Pollen–Specific Gene Expression in Transgenic Plants: Coordinate Regulation of Two Different Tomato Gene Promoters During Microsporogenesis", *Development*, (1990), 109:705–713.

Mihaly Czako et al., "Differential Manifestation of Seed Mortality Induced by Seed–Specific Expression of the Gene for Diphtheria Toxin A Chain in Arabidopsis and Tobacco", *Mol. Gen Genet*, (1992) 235:33–40.

van der Geest, Apolonia H.M., et al., "Cell Ablation Reveals That Expression from the Phaseolin Promoter is Confined to Embryogenesis and Microsporogenesis", *Plant Physiol*, (1995) 109:1151–1158.

Koning, Ann et al., "Arrest of Embryo Development in *Brassica napus* Mediated by Modified *Pseudomonas aeruginosa* Exotoxin A", *Plant Molecular Biology* (1992) 18:247–258.

Sitbon, Folke et al., "Tansgenic Tobacco Plants Coexpressing the *Agrobacterium tumefaciens* iaaM and iaaH Genes Display Altered Growth and Indoleacetic Acid Metabolism", *Plant Physiol* (1992) 99:1062–1069.

[ABSTRACT 161] Nir, Canni Two Approaches to Genetically Engineered Parthenocarpy Rivka Barg, *Dept. Plant Genet*, The Volcani Center, Aro, Bet–Dagan 50250 Israel; Inst. Plant Genet., Slovak Acad Sci. Nitra 94902, Slovak Rep.

Vivekananda, Jeevalatha, "Hormonal and Environmental Regulation of the Carrot Lea–Class Gene Dc3", *Plant Physiol* (1992) 100:576–581.

Bensen et al. Cloning and characterization of the maize An1 gene. The Plant Cell, vol. 7, 75–84, Jan. 1995.

Napoli et al. Introduction of a chimeric chalcone synthase gene into Petunia results in reversible co–wupression of homologous genes in trans. The Plant Cell, vol. 2, 279–289, Apr. 1990.

*Primary Examiner*—Douglas W. Robinson
*Assistant Examiner*—Thomas Haas
*Attorney, Agent, or Firm*—Zarley, McKee, Thomte, Voorhees, & Sease

[57] ABSTRACT

The invention discloses a transgenic method for producing parthenocarpic fruits or fruits with reduced seed number. It involves the temporal expression of a plant hormone or precursor or other such gene so that gibberellin or other similar hormonal activity involved in initiating fruit set activity is potentiated. The gene is operably linked to a regulatory promoter so that expression is timed prior to pollen development or fertilization. Expression of the hormone causes fruit development in the absence of fertilization. The method also results in a fruit that has diminished or very little seed. The invention also includes transgenic constructs, vectors, and methods for production of the parthenocarpic plants.

26 Claims, No Drawings

TRANSGENIC METHODS AND COMPOSITIONS FOR PRODUCING PARTHENOCARPIC FRUITS AND VEGETABLES

FIELD OF THE INVENTION

This invention relates generally to the field of plant molecular biology and in particular to transgenic plants, seeds, and tissues which have been genetically modified to create plants that will bypass the need for fertilization and initial fruit set regardless thereof will produce seedless fruits and vegetables in a variety of growing conditions.

BACKGROUND OF THE INVENTION

In angiosperm plants, fruit develops from the pericarp which surrounds the developing seed. The development of fruit occurs after pollination and fertilization, which results in production of an embryo. Upon male gamete fusion with other cells in the ovule the endosperm is initiated, and develops concomitant with proliferation of the protoplast embryo. As the ovules develop into seeds the ovary swells into fruit. Ordinarily fruit development in non apomicytic species is triggered by fertilization of the ovules, and if pollination or fertilization does not occur then flower abscission occurs and no fruit is set.

Fruit set is also hindered by external factors such as temperature fluctuation, water availability, and light conditions, For example, peppers are very sensitive to temperature fluctuations. A temperature of less than 50° F. at night or greater than 80° during the day will cause fruit not to set after pollination. Smaller variations will lead to uneven fruit set resulting in abnormally shaped fruit. The ability to control the initiation of fruit set in plants could avoid these problems as fruit set could be controlled internally regardless of external factors, thereby improving yield as well as potential growing areas. Such control could also provide for initiation of fruit set without fertilization i.e. the production of a parthenocarpic phenotype. This can allow for development of fruit by a plant species regardless of external factors and can provide for fruit development regardless of even fertilization. Often the parthenocarpic phenotype not only allows for fruit set without fertilization, but without fertilization, seed development is minimized or is inhibited completely, providing a second benefit of parthenocarpy.

Seedless fruits and vegetables have long been a goal of those in the field of produce. Benefits of such plants include the obvious appeal to consumers for ease in preparing and consuming such produce. Other benefits include a sweeter, fleshier fruit or vegetable, and an increase in edible portion as the seed cavity is absent or greatly reduced. Several advances have been made in this field, usually with topical application of hormones or with highly complex breeding procedures resulting in a triploid genotype.

Topical applications of gibberellin has long been used to induce a seedless (parthenocarpic) phenotype in grapes. This method usually requires a spraying procedure which is cumbersome, weather dependent, and must be timed correctly to occur immediately after pollination.

Another method requires a complex breeding procedure for production of seedless watermelons. The seedless condition in watermelon is almost always the result of the presence of three homologous complements per cell rather than the usual two, known as triploid. These watermelons have problems in developing normally into an embryo and causes absence of seeds in the triploid plants. The abnormal embryo formation causes the cessation of normal ovular development into a seed at an early stage. Typically seedless watermelons contain small edible white ovules similar to those in immature cucumbers.

A transgenic method of creating seedless fruit is disclosed in World Patent WO91/09957. It involves a highly complex recombination excision system termed, "CRE-LOX". Generally the gene product of CRE produces a protein recombinase which acts at the specific LOX DNA sequence. Several recombination functions are disclosed with the most consistent being excision of the LOX DNA sequence. Seedless watermelons are hypothesized in the application to occur under the conditions involving transformation with the barnase gene derived from *Bacillus amyloliquefaciens*. Generally the female has a seed coat specific promoter (SC):CRE:terminator the male has a SC promoter:barnase gene::lox::barnase gene:terminator. There are no phenotype changes in the two parents when propagated and in the seed production field the female seed parent has normal seed set because both genes are not functioning at the same time (seed coat is only maternal tissue). However in the F1 generation the maternal tissue will contain both genes. In this configuration the constitution of the seed coat (F1 plant, F2 seeds) is SC promoter:barnase gene::-::barnase gene:terminator where ::-:: represents the point where the lox gene is excised making a functional toxin gene specific to the seed coat. In theory if the seed coat breaks down the development of the seed will be arrested because of lack of nutrient flow to the embryo.

No experimental data is disclosed and the success of the proposed protocol in development of actual seedless watermelon is nowhere shown.

Thus it can be seen from the foregoing that a need exists in the art for production protocols for parthenocarpic fruits and vegetables which are simple, straightforward and easily repeatable.

It is an object of the present invention to provide expression constructs which when expressed in a transgenic plant result in fruit set without fertilization and also results in production of seedless fruits and vegetables.

It is yet another object of the invention to provide inbred parental lines which can be crossbred resulting in an F1 plant which will be parthenocarpic and will produce no seeds or a significant reduction in the amount of seeds present.

It is yet another object of this invention to provide plants, plant cells and plant tissues containing the expression constructs of the invention.

It is yet another object of the invention to provide vehicles for transformation of plant cells including viral or plasmid vectors and expression cassettes incorporating the genes and promoters of the invention.

It is yet another object of the invention to provide bacterial cells comprising such vectors for maintenance replication and plant transformation.

Other objects of the invention will become apparent from the description of the invention which follows.

SUMMARY OF THE INVENTION

In one embodiment the invention comprises genetic manipulation of plants to potentiate the effects of gibberellin or other hormones involved in initiation of fruit set. The invention comprises the temporal expression of a structural gene which encodes a plant hormone such as (gibberellins, or cytokines) or proteins associated with the production of such hormones (i.e. enzymes, biosynthetic intermediates etc.) which are associated with initiation of fruit set. The structural gene is placed under the control of a pollen microspore or megaspore specific promoter such that expression of the hormone is timed to occur just prior to pollination so that fruit development and maturation is induced without the need for fertilization.

DETAILED DESCRIPTION OF THE INVENTION

The topical use of exogenous hormones to either aid in fruit set, or in some cases to induce parthenocarpy are well established in fruit and vegetable growing areas. Use of the auxin inhibitor Tomaset (N-meta-tolyl-phthalamic acid, or 4-CPA) to induce parthenocarpy of tomato under cool conditions in greenhouses has been previously accomplished. Pepper growers in Florida use a GA application to improve fruit set during the growing season. Grapes are routinely treated with gibberellins to induce fruit set, enlarge cluster size, and uniform fruit growth, especially for seedless types. See for example, Jankiewicz, L. S., Flores, A. E., Gorecki, R., Staniaszek, M, "Effect of growth regulators on parthenocarpic fruit set in Capsicum annum". Additional gibberellin treatment is used to assure that new fruit is set as older fruit matures and is harvested. See, SO: Folia-Horticulturae (Poland), (1991), v. 3(2), p. 3–16.

In the description that follows a number of terms are used extensively. The following definitions are provided in order to remove ambiguities in the intent or scope of their usage in the specification and claims, and to facilitate understanding of the invention.

As used herein the term gibberellin shall include any product which possesses the biologic activity of a gibberellin and can include gibberellin-like proteins which possess homology to a gibberellin product such that its biologic activity is maintained by mutation studies discussed hereinafter.

As used herein the term fruit shall include any angiospermiplant which has its pollen and ovule producing organs in flowers; with ovules enclosed in an ovary, and after fertilization with each ovule developing into a seed while the vary expands into a fruit. Any such fruit which is desirabie of being produced in a parthenocarpic manner is encompassed by this definition. Further, food sources traditionally considered vegetables but which are produced in this manner are also intended to be encompassed such as tomatoes, peppers and the like.

A promoter is a DNA sequence that directs the transcription of a structural gene. Typically a promoter is located in the 5' region of a gene, proximal to the transcriptional start site of a structural gene.

A pollen specific promoter is any promoter capable of regulating temporal expression at a time prior to or soon after pollination so that fruit development and maturation is induced without significant seed development. Such promoters as delineated herein include but are not limited to inducible promoters, microspore or megaspore promoters, pollen specific promoters, or maternal tissue promoters such as seed coat promoters or any other promoter associated with a gene involved in pollination or ovule maturation or development.

A structural gene is a DNA sequence that is transcribed into messenger RNA (mRNA) which is then translated into a sequence of amino acids characteristic of a specific polypeptide. The term expression refers to biosynthesis of a gene product. In the case of a structural gene expression involves transcription of the structural gene into MRNA and then translation of the MRNA into one or more polypeptides.

A cloning vector is a DNA molecule such as a plasmid, cosmid or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

An expression vector is a DNA molecule comprising a gene that is expressed in a host cell. Typically gene expression is placed under the control of certain regulatory elements including promoters, tissue specific regulatory elements, and enhancers. Such a gene is said to be "operably linked to" the regulatory elements.

A recombinant host may be any prokaryotic or eukaryotic cell that contains either a cloning vector or an expression vector. This term also includes those prokaryotic or eukaryotic cells that have been genetically engineered to contain the cloned genes in the chromosome or genome of the host cell.

A transgenic plant is a plant having one or more plant cells that contain an expression vector.

Plant tissue includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plant or in organ, tissue or cell culture.

Molecular Transformation Techniques

Production of a genetically modified plant tissue expressing a structural gene under the control of regulatory promoters combines teachings of the present disclosure with a variety of techniques and expedients known in the art. In most instances alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural hormone gene selection are other parameters which may be optimized to achieve desired plant expression as is known to those of skill in the art and taught herein.

The selection of an appropriate expression vector will depend upon the method of introducing the expression vector into host cells. Typically an expression vector contains (1) prokaryotic DNA elements coding for a bacterial replication origin and an antibiotic resistance marker to provide for the growth and selection of the expression vector in a bacterial host; (2) DNA elements that control initiation of transcription such as a promoter; (3) DNA elements that control the processing of transcripts such as transcription termination/polyadenylation sequence; and (4) a reporter gene that is operably linked to the DNA elements to control transcription initiation. Useful reporter genes include β-glycuronidase, β-galactosidase, chloramphenicol acetyl transferase, luciferase, and the like. Preferably the reporter gene is either β-glycuronidase (GUS) or luciferase.

The general descriptions of plant expression vectors and reporter genes can be found in Gruber, et al., "Vectors for Plant Transformation, in Methods in Plant Molecular Biology & Biotechnology" in Glich et al., (Eds. pp. 89–119, CRC Press, 1993). Moreover GUS expression vectors and GUS gene cassettes are available from Clone Tech Laboratories, Inc., Palo Alto, Calif. while luciferase expression vectors and luciferase gene cassettes are available from Pro Mega Corp. (Madison, Wis.).

Expression vectors containing genomic or synthetic fragments can be introduced into protoplast or into intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, Glich et al. (Eds. pp. 67–88 CRC Press, 1993); and by Phillips et al. "Cell-Tissue Culture and In-Vitro Manipulation" in Corn & Corn Improvement, 3rd Edition Sprague et al. (Eds. pp. 345–387) American Society of Agronomy Inc. et al. 1988.

Methods of introducing expression vectors into plant tissue include the direct infection or co-cultivation of plant cell with *Agrobacterium tumefaciens,* Horsch et al., Science, 227:1229 (1985). Descriptions of agrobacterium vector systems and methods for agrobacterium-mediated gene transfer provided by Gruber, et al. supra.

Preferably, expression vectors are introduced into plant tissues using a direct gene transfer method such as micro projectile-mediated delivery, DNA injection, electroporation and the like. More preferably expression vectors are introduced into plant tissues using the micro projectile media delivery with the biolistic device.

The invention comprises use of these types of transformation procedures to generate a plant in which fruit set is induced prior to fertilization resulting in a parthenocarpic plant which also will contain little or no seed. This is of particular value for plants in which fruit set is easily inhibited by external factors such as temperature fluctuations, rain fall etc. A construct comprising a hormone which stimulates fruit set and development, or which comprises a gene which encodes a protein that promotes production of such a hormone (a precursor molecule or enzyme) operably linked to a pollen specific promoter is introduced to said plant.

In a preferred embodiment the invention comprises use of a structural gene which promotes the synthesis of or encodes any of the family of gibberellin or gibberellin-like plant hormones.

The methods of the invention described herein may be applicable to any species of angiosperm the fruit or vegetable of which is desirable to produce at a wide range of conditions without a negative impact on fruit set and development and within which it is desirable to make seedless. Fruits and vegetable plants which can be made seedless according to the methods of the invention include but are not limited to include, melons such as watermelon, and musk melon, berries such as strawberries, and blueberries, peppers such as green peppers, red bell peppers, yellow peppers, tomatoes, oranges, plums, alfalfa, squash, eggplant, sweetcorn, peas, cotton, avocados, mangos, papayas, nectarines, apples, grapefruit, lemons, limes, tangerines, pears and peaches. In a preferred embodiment the inventions is used with fruits such as peppers, in which fruit set is very sensitive to external conditions. The methods of the invention will be illustrated below with reference to particular embodiments.

A plant hormone which is critical to fruit set and development is one which includes hormones which are critical to pollen, microspore, macrospore or embryo formation and/or function and includes proteins or enzymes that are instrumental in the development of fruit, including cells and/or tissues from which fruit develops, cells and/or tissues which form part of the ovary, endosperm, pericarp or embryo or other female structure in which fruit develops after, fertilization.

The DNA sequence may be any identifiable DNA sequence encoding gene products which are capable of inducing fruit set and development in a cell or a plant. Examples of such a DNA sequence include hormones such as gibberellin, auxins, etc., precursors to such hormones, or enzymes involved in biosynthesis of such hormones.

Gibberellins (GAs) are a family of diterpenoid plant growth hormones some of which are bioactive growth regulators. GAs are required for controlling such diverse processes as seed germination, cell elongation and division, leaf expansion, stem elongation, flowering, and fruit set. GAs have been the subject of many physiological, and biochemical studies, and a variety of plant mutants with altered patterns of GA biosynthesis or response have been studied (Graebe, J. E., Ann. Rev. Plant Physiol. 38:419–465 (1987)).

Extensive biochemical studies on endogenous GA intermediates in GA-responsive dwarf mutants have allowed the determination of the GA biosynthetic pathway and several genetic loci involved in GA biosynthesis (reviewed by Graebe, J. E., Ann. Rev. Plant Physiol. 38:419–465 (1987). A number of the GA responsive dwarf mutants have been isolated from various plant species, such as maize, pea, and Arabidopsis (Phinney, B. O. et al., "Chemical Genetics and the Gibberellin Pathway" in Zea mays L. in Plant Growth Substance, ed., P. F. Waering, New York: Academic (1982) pp. 101–110; Ingram, T. J. et al., Planta 160:455–463 (1984); Koornneef, M., Arabidopsis Inf. Serv. 15:17–20 (1978)). The dwarf mutants of maize (dwarf-1, dwarf-2, dwarf-3, dwarf-5) have been used to characterize the maize GA biosynthesis pathway by determining specific steps leading to biologically important metabolites (Phinney, B. O. et al, "Chemical Genetics and the Gibberellin Pathway" in Zea mays L. in Plant Growth Substance, ed., P. F. Waering, New York: Academic (1982) pp. 101–110; Fujioka, S. et al., Plant Physiol. 88:1367–1372 (1988)). Similar studies have been done with the dwarf mutants from pea (Pisum sativum L.) (Ingram, T. J. et al., Planta 160:455–463 (1984)). GA deficient mutants have also been isolated from Arabidopsis (ga1, ga2, ga3, ga4, ga5)(Koornneef, M., et al., Theor. Appl. Genet. 58:257–263 (1980)). One of the most extensive genetic studies of GA mutants has been carried out by Koornneef et al. (Theor. Appl. Genet. 58:257–263 (1980); Koornneef et al., Genet. Res. Camb. 41:57–68 (1983)) in the crucifer, Arabidopsis thaliana. Using ethylmethane sulfonate (EMS) and fast neutron mutagenesis, Koornneef has isolated nine alleles mapping to the GA1 locus of A. thaliana (Koornneef et al. (Theor. Appl. Genet. 58:257–263 (1980); Koornneef et al., Genet. Res. Camb. 41:57–68 (1983)).

Structural genes useful for the method of the invention include genes which encode gibberellin or a biosynthesis gibberellin intermediate such as an enzyme or precursor which is eventually converted to gibberellin.

In yet another embodiment, the gibberellin receptor may be mutated to cause it to be more sensitive to gibberellin.

One example of a gene useful in practice of the invention includes that disclosed in European Patent Application EPO 692537A2 by Tai-Ping Sun et al., "Recombinant Gibberellin DNA and Uses Thereof", the disclosure of which is incorporated herein by reference. The publication discloses the cDNA and genomic DNA corresponding to the GA1 locus of Arabidopsis thaliana which encodes ent-Kaurene synthetase.

The enzyme encoded by the GA1 gene is involved in the conversion of GGPP to ent-Kaurene (Barendse and Koornneef, Arabidopsis Inf. Serv. 19:25–28 (1982); Barendse et al., Physiol. Plant. 67:315–319 (1986); Zeenvaart, J. A. D., in Plant Research '86, Annual Report of the MSU-DOE Plant Research Laboratory, 130–131 (East Lansing, Mich., 1986)), a key intermediate in the biosynthesis of GAs (Graebe, J. E., Ann. Rev. Plant Physiol. 38:419–465 (1987)). Ent-kaurene synthetase has only been partially purified from a variety of plants (Duncan, Plant Physiol. 68:1128–1134 (1981)).

The synthesis of GGPP from mevalonate is common in terpenes. GGPP is a branch point metabolite which is not only the precursor of GAs, but also a precursor of other diterpenes, such as the phytol chain of chlorophylls, and tetraterpenes, such as the carotenoids. The first committed step of the GA pathway is the conversion of GGPP to entkaurene in a two-step cyclization reaction. GGPP is partially cyclized to the intermediate, copalyl pyrophosphate (CPP), by ent-kaurene synthetases A and CPP is immediately converted to ent-kaurene by ent-kaurene synthetase B. Since ent-kaurene is a key intermediate in the GA pathway, its synthesis is likely to be a regulatory point for GA biosynthesis. Indeed, ent-kaurene production has been shown to be altered by changes in photoperiod, temperature, and growth potential of tissues in certain species (Chung and Coolbaugh, 1986; Moore and Moore, 1991; Zeevaart and Gage, 1993).

By examining the molecular lesions in several GA1 alleles, a direct correlation of the genetic and physical maps of the GA1 locus was established and a recombination rate of $10^{-5}$ cM per nucleotide was determined for this region of the A. thaliana genome. (Koornneef, Genet. Res. Comb. 41:57–68 (1983)).

Another example of a gene useful for practice of the invention includes that disclosed in PCT publication WO94/28141 by Theodor Lange et al., "Regulation of Plant Growth", the disclosure of which is incorporated herein by reference. This application discloses the molecular cloning of the gene encoding gibberellin (GA) 20- oxidase and its use. (GA)20 oxidase is a regulatory enzyme and GA production is particularly sensitive to its activity. Expression of the enzyme increases levels of biologically active gibberellins.

Yet other structural genes useful for the invention includes either the AN1 or AN2 gene disclosed in WO95 35383 "Plant anther ear genes encoding cyclase affect gibberellic acid biosynthesis—useful for altering height and fertility in monocotyledons" by Benson, R. J. et al., the disclosure of which is incorporated herein by reference. The publication discloses the cloning and expression anther ear 1 (AN1) and anther ear 2 (AN2) genes cloned from maize. The gene product affects the conversion of GGPP to ent-kaurene in the biosynthesis of gibberellic acid.

A Tomato GA deficient mutant is abnormal, and the result is misshapen fruit. This phenotype can be overcome by the application of bioactive GAs. Tomato mutations include gib1, gib2, gib3, none of which have been cloned. The tomato mutation gib1 is the metabolic equivalent of AN1 in corn. The observation that addition of bioactive GA to developing fruit of gib1, gib2 and gib3 suggests that expression of a structural gene that makes bioactive GA would offset abnormal fruit set and shape in pepper and other fruits. Similar observations have been made in Arabidopsis. In Arabidopsis the gene GA1 is the metabolic equivalent of AN1 in corn, and has been cloned and sequenced. In peas removal of seeds at an early stage lead to abnormal pod development since the source of bioactive GA is the seed.

Thus the invention in a preferred embodiment includes the AN1 or AN2 genes which have gibberellin-like activity to achieve the parthenocarpic phenotype. Loss of AN1 reduces the amount of metabolic product by 80% of the total produced. The contribution of AN2 of the remaining 20% has yet to be determined. AN2 is an expressed gene with high homology to AN1 (70% identical). Both genes are disclosed in WO95/35383, the disclosure of which has been previously incorporated by reference.

There is approximately 50–60% identity at the amino acid level between AN1 and the GA1 genes. The AN1 sequence has been used to recover similar sequences in rice. A comparison of the maize and Arabidopsis sequences could be used to derive a consensus sequence that would be useful in isolating similar genes in pepper or other species for practice of the invention.

Another potential gene includes the GA4 gene from Arabidopsis. These gene products catalyze the last step in the gibberellin biosynthetic process which makes bioactive GA1.

Gibberellic acids are synthesized from the isoprenoid GGPP, beginning with the cyclizations of GGPP to CPP, then CPP to ent-kaurene, catalyzed by kaurene synthetase A and B, respectively (Duncan et al., 1981). Most higher plants are thought to be like maize in that, in maize, ent-kaurene is oxidized stepwise to 7-hydroxy-kaurenoic acid, which is converted to the first true gibberellin; GA12-aldehyde (Suzuki et al., 1992). The latter compound then is oxidized further to an active GA by one of three parallel pathways. In maize the dominant pathway appears to be the early 13-hydroxyl pathway (Hedden et al., 1982), with GA1 being the penultimate, active product, typically present in less than 1 ug/100 gfwt amounts (Fujioka et al., 1988).

The homology between predicted amino acid sequences of maize AN1 and Arabidopsis GA1 points to a common function for these genes. Their overall identity of 47% (68% similarity) is striking, but is even stronger in an internal 300 amino acid segment that is 68% identical (94% similar). As to the putative polyprenyl-pyrophosphate binding domain within this segment, AN1 and GA1 share 100% similarity. Other sequenced plant genes that use polyprenylpyrophosphorylated substrates (geranyl-, farnysyl- and geranylgeranyl-pyrophosphate) also share significant homology with AN1 in this domain (Facchini et al., 1992), but much less overall homology with AN1 (20 to 25% identity). These sequence homologies clearly indicate that AN1 encodes a cyclase which functions in the conversion of GGPP to ent-kaurene.

The promoters used in the methods of the invention may be a pollen specific promoter, a maternal tissue promoter an inducible promoter or a constitutive promoter. It will be appreciated that the term pollen used herein and in particular with reference to the inducible promoter described in the disclosure and claims, includes cells and/or tissues from which pollen develops (e.g. pre meiotic and uninucleate microspore cells), cells and/or tissues which form part of the male structure in which pollen develops (e.g. anther, tapetum or filament) and pollen itself. Also included are any promoters which will correlate expression with the early initiation of plant reproduction as the plant progresses beyond the vegetative state. This can include promoters associated with fertilization, or the fertile plant including all sexual organs, as well as early seed development promoters.

The pollen-specific promoter used is may be selected from the group of promoters known to direct expression in the anther, tapetum, filament, pollen itself or in corresponding ovary, endosperm pericarp or embryo structures.

Examples of pollen specific promoters include those disclosed in U.S. Pat. No. 5,086,169 to Mascarenhas which discloses a pollen specific promoter isolated from maize; U.S. Pat. No. 5,412,085 to Allen et a., which discloses another pollen specific promoter from maize; U.S. Pat. No. 5,477,002 to Tuttle et al., which discloses an anther specific promoter; U.S. Pat. No. 5,470,359 to Huffman et al., which discloses a tapetum specific promoter; WO92 11379 to Draper et al which discloses a tapetum specific promoter isolated from Brassicaceae, Plant, July 1995 8(1) p. 55–63, which discloses a pollen specific promoter from tobacco and Plant Mol. Biol. Jan. 1992 18(2) p. 211–8, discloses yet another pollen specific promoter from maize. These are just some examples of promoters which could be used, and the invention is not limited to these. Other such promoters are known to those of skill in the art, and are intended to be encompassed within the scope of the invention. The disclosure of all of the foregoing are incorporated herein by reference.

Other useful promoters include any promoter which can be derived from a gene whose expression is maternally associated with the embryo and or endosperm or early pollen formation.

The preferred promoters may be used in conjunction with naturally occurring flanking coding or transcribed sequences of the seed specific genes or with any other coding or transcribed sequence that is critical to seed formation and/or function.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to seed formation and/or function.

Additionally regions of one promoter may be joined to regions from a different promoter in order to obtain the desired promoter activity resulting in a chimeric promoter. Synthetic promoters which regulate gene expression to seed development may also be used.

The promoter used in the method of the invention may also be an inducible promoter. An inducible promoter is a promoter that is capable of directly or indirectly activating transcription of a DNA sequence in response to an inducer. In the absence of an inducer the DNA sequence will not be transcribed. Typically the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 KD heat shock promoter of D. melanogaster (Freeling, M., Bennet, D. C., Maize ADN 1, Ann. Rev. of Genetics 19:297–323) and the alcohol dehydrogenase promoter which is induced by ethanol (Nagao, R. T., et al., Miflin, B. J., Ed. Oxford Surveys of Plant Molecular and Cell Biology, Vol. 3, p. 384–438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

In a preferred embodiment the promoter is one which is maternal tissue specific such as a seed coat specific, one which is expressed only in maternal tissue such as the a' subunit of β-conglycinin of soybean (a'-β- C6) which is highly expressed in early seed development in the endosperm and embryo described in J. Biol. Chem. 261:9228 (1986), incorporated herein by reference.

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl=2-chloro-4-(trifluoromethyl)-5-thiazolecarboxylate (common name: flurazole). In addition a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The promoter may be a constitutive promoter. A constitutive promoter is a promoter that functions in all, many, or a variety of cell types including cells/tissues critical to pollen formation and/or function. An example of such a constitutive promoter is CaMV 35S or preferably HP 101 which has been isolated from *Brassica napus*.

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by testing in vitro phosphorylation of kanamycin using techniques described in the literature or by testing for the presence df the MRNA coding for the NPT II gene by Northern blot analysis in RNA from the tissue of the transformed plant. Transformed plant cells thus selected can be induced to differentiate into plant structures which will eventually yield whole plants. It is to be understood that a selection marker gene may also be native to a plant.

A recombinant DNA molecule containing any of the DNA sequences and promoters described herein may be integrated into the genome of the male sterile plant or second plant by first introducing a recombinant DNA molecule into a plant cell by any one of a variety of known methods. Preferably the recombinant DNA molecule(s) are inserted into a suitable vector and the vector is used to introduce the recombinant DNA molecule into a plant cell.

The use of Cauliflower Mosaic Virus (CaMV) (Howell, S. H., et al, 1980, Science 208:1265) and gemini viruses (Goodman, R. M., 1981, J. Gen Virol. 54:9) as vectors has been suggested but by far the greatest reported successes have been with Agrobacteria sp. (Rorsch, R. B., et al, 1985, Science 227:1229–1231). Methods for the use of Agrobacterium based transformation systems have now been described for many different species. Generally strains of bacteria are used that harbor modified versions of the naturally occurring Ti plasmid such that DNA is transferred to the host plant without the subsequent formation of tumors. These methods involve the insertion within the borders of the Ti plasmid the DNA to be inserted into the plant genome linked to a selection marker gene to facilitate selection of transformed cells. Bacteria and plant tissues are cultured together to allow transfer of foreign DNA into plant cells then transformed plants are regenerated on selection media. Any number of different organs and tissues can serve as targets from Agrobacterium mediated transformation as described specifically for members of the Brassicaceae. These include thin cell layers (Charest, P. J., et al, 1988, Theor. Appl. Genet. 75:438–444), hypocotyls (DeBlock, M., et al, 1989, Plant Physiol. 91:694–701), leaf discs (Feldman, K. A., and Marks, M. D., 1986, Plant Sci. 47:63–69), stems (Fry J., et al, 1987, Plant Cell Repts. 6:321–325), cotyledons (Moloney M. M., et al, 1989, Plant Cell Repts 8:238–242) and embryoids (Neuhaus, G., et al, 1987, Theor. Appl. Genet. 75:30–36). It is understood, however, that it may be desirable in some crops to choose a different tissue or method of transformation.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

Other methods that have been employed for introducing recombinant molecules into plant cells involve mechanical means such as direct DNA uptake, liposomes, electroporation (Guerche, P. et al, 1987, Plant Science 52:111–116) and micro-injection (Neuhaus, G., et al, 1987, Theor. Appl. Genet. 75:30–36). The possibility of using micro projectiles and a gun or other device to force small metal particles coated with DNA into cells has also received considerable attention (Klein, T. M. et al., 1987, Nature 327:70–73).

It is contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

As indicated above, it may be desirable to produce plant lines which are homozygous for a particular gene. In some species this is accomplished rather easily by the use of anther culture or isolated microspore culture. This is especially true for the oil seed crop Brassica napus (Keller and Armstrong, Z. flanzenzucht 80:100–108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

A number of different ways of producing the hormone molecule specifically timed to pollen, or fertilization development can be envisioned. In all approaches, at least one step in the production of the hormone molecule has to take place specifically within a tissue involved in pollination and fertilization at a time just prior thereto to induce the plant to proceed with fruit set.

Any number of genes could be used to carry out the process and methods of the invention providing that the simultaneous production of two or more enzymatic or synthetic activities specifically in the plant leads to potentiation of gibberellin timed prior to fertilization and seed development. This implies that any intermediate in gibberellin biosynthesis could be used, as well as enzymes catalyzing these reactions or even receptors activated by the presence of gibberellin. In yet another embodiment the gene could be an antisense oligonucleotide which will interfere and prevent transcription of an enzyme which degrades or inhibits gibberellin.

As can be seen, several combinations of structural genes and pollen development specific promoters are contemplated within the scope of the invention.

A highly desirable seedless system is one in which fully fertile F1 seed develops, that can then be grown into plants that produce only seedless fruit. This system is economically favorable in that for each cross pollination, a large number of seedless fruits result: the number of F1 seed from one cross X the number of fruits produced on an F1 plant. Also incorporated in this scheme are the advantages of growing a hybrid crop, including the combining of more valuable traits and hybrid vigor. This is accomplished in the same manner as described above except that the hormone gene is expressed from an inducible, or repressible promoter. This will allow for generation of parental lines which will carry but will not express the gene. The F1 hybrid between the two will thus have the gene as well and upon application of an agent which will induce expression, will become parthenocarpic. With a repressible promoter the F1 parents will express the gene but it will be repressed in the female used for seed production. Use of temperature specific promoters, or suppressible promoters can also be used to generate F1 hybrids.

The essence of the parthenocarpic phenotype is expression of gibberellin near or at the time of pollination which should induce the a signal that seed production has been initiated. Seed set and early seed growth is responsible for fruit set and normal maturation of fruit in pepper and other fruits and vegetables.

Another approach is to modify the receptor to GA to increase sensitivity to endogenous GA levels. The SPY1 gene product is involved in GA signal transduction, i.e. a receptor for GA. A combination of a modified receptor for GA and fruit specific promoters could be used to modify fruit phenotype analogous to the use of genes which result in higher levels of bioactive GA.

What is claimed is:

1. An expression construct for production of transgenic parthenocarpic plants comprising:
   a recombinant gene which encodes upon expression a plant hormone, precursor thereof or enzyme involved in biosynthesis thereof, wherein said hormone promotes fruit set and/or development and
   a pollen specific promoter operably linked to said gene.

2. The expression construct of claim 1 wherein said plant hormone is gibberellin.

3. The expression construct of claim 2 wherein said plant hormone is gibberellin oxidase.

4. The gene construct of claim 1 wherein said gene is Anther Ear 1.

5. The gene construct of claim 1 wherein said gene is Anther Ear 2.

6. The expression construct of claim 1 wherein said plant is a pepper plant.

7. The expression construct of claim 1 wherein said promoter is an inducible promoter.

8. A nucleic acid vector comprising the expression construct of claim 1.

9. The vector of claim 8 wherein said vector is a cloning vector.

10. The vector of claim 8 wherein said vector is an expression vector.

11. The vector of claim 8 further comprising a marker gene for selection of transformed cells.

12. The vector of claim 11 wherein said marker gene is selected from the group consisting of an ampicillin resistance gene, a tetracycline resistance gene and a hygromycin resistance gene.

13. The vector of claim 8 further comprising a polyadenylation signal.

14. A prokaryotic or eukaryotic host cell transformed with the nucleic acid vector of claim 7.

15. A transgenic plant comprising a plant cell or ancestor of said plant cell which has been transformed with the vector of claim 8.

16. A parthenocarpic fruit produced by a plant which contains a DNA sequence encoding a recombinant gene which encodes a plant hormone which initiates fruit set or development, a precursor of said hormone, or enzyme involved in synthesis of said hormone, said gene operably linked to a pollen specific promoter so that expression occurs prior to pollination.

17. A method of producing parthenocarpic fruits comprising:
   transforming an angiosperm plant cell with a DNA sequence which encodes a plant hormone involved in initiation of fruit set or a precursor of said hormone or an enzyme involved in synthesis of said hormone operably linked to a pollen specific promoter; and
   generating a plant from said transformed cell; wherein said plant is parthenocarpic and fruit set is initiated without pollination.

18. The method of claim 17 wherein said plant is selected from the group consisting of a melon plant, a pepper plant, and a tomato plant.

19. The method of claim 17 wherein said DNA sequence encodes gibberellin oxidase.

20. The method of claim 19 wherein said promoter is selected from the group consisting of: a constitutive promoter, an inducible promoter, and a maternal tissue promoter.

21. A method of producing a hybrid parthenocarpic plant said method comprising
   pollinating a parent plant which has been transformed or which ancestor thereof has been transformed with a DNA sequence which encodes a plant hormone gene product operably linked to an inducible promoter;
   with a second parent plant which has been transformed or whose ancestor has been transformed with a similar gene, said DNA sequence operably linked to an inducible promoter, so that upon application of the inducer the plant will become parthenocarpic.

22. A method of producing parthenocarpic fruits and vegetables comprising:
   transforming a plant cell or an ancestor thereof with a DNA sequence which will potentiate gibberellin expression, said sequence regulated by a pollen specific promoter; and
   generating a parthenocarpic plant from said cell.

23. The method of claim 22 wherein said DNA sequence is a structural gene.

24. The method of claim 23 wherein said gene is a gibberellin receptor.

25. The method of claim 23 wherein said gene encodes upon expression gibberellin oxide.

26. A method of producing parthenocarpic fruits comprising:

transforming an angiosperm plant cell with a DNA sequence which encodes a plant hormone involved in initiation of fruit set or a precursor of said hormone or an enzyme involved in synthesis of said hormone operably linked to a pollen specific promoter wherein said hormone is auxin; and generating a plant from said transformed cell; wherein said plant is parthenocarpic and fruit set is initiated without pollination.

* * * * *